United States Patent [19]

Depp et al.

[11] 4,436,420

[45] Mar. 13, 1984

[54] OPTICAL FLUID ANALYZING APPARATUS AND METHOD

[75] Inventors: Steven W. Depp; Glenn T. Sincerbox, both of San Jose, Calif.

[73] Assignee: International Business Machines Corporation, Armonk, N.Y.

[21] Appl. No.: 307,269

[22] Filed: Sep. 30, 1981

[51] Int. Cl.³ ............................................ G01N 21/41
[52] U.S. Cl. .................................... 356/128; 356/361
[58] Field of Search ....................... 356/128, 135, 361; 350/162.17

[56] References Cited

U.S. PATENT DOCUMENTS 3,499,712 3/1970 Kottle et al. ........................ 356/128
4,188,123 2/1980 Kleinknecht ........................ 356/128

OTHER PUBLICATIONS

Levi, Leo. *Applied Optics; A Guide to Optical System Design*/vol. 2, Wiley & Sons, New York, copyright 1980, pp. 268-271.
"Diffraction Refractometer" by A. B. Nafarrate, IBM Technical Disclosure Bulletin, vol. 13, No. 1, Jun. 1970.
"Fundamentals of Optics" by F. A. Jenkins et al., McGraw-Hill Book Co., Inc., 1957, Third Edition.

*Primary Examiner*—R. A. Rosenberger
*Attorney, Agent, or Firm*—Henry E. Otto, Jr.

[57] ABSTRACT

An optical fluid analyzing apparatus is shown comprising transparent means (12,13) of known refractive index ($n_1$) providing a cell (14) for receiving a fluid sample of unknown refractive index ($n_2$). A diffraction grating 10 is formed in an inner wall (11) of the cell. A light source (15) is positioned at an incident angle ($\theta_0$) with a grating to satisfy the Bragg condition. A pair of detectors (16, 17) intercept the 0th order and 1st order diffracted light. Circuitry (18) responds to signals generated by the detectors to provide an output indicative of the refractive index of the sample.

7 Claims, 2 Drawing Figures

OPTICAL FLUID ANALYZING APPARATUS AND METHOD

BACKGROUND OF THE INVENTION

This invention relates to an optical analyzing apparatus and method for measuring the refractive index of a fluid sample.

Various techniques have heretofore been proposed to measure the refractive index of a liquid or gas. One technique employs a prism and requires the measurement of a critical angle. In "Fundamentals of Optics", Jenkins and White Third Edition, published by McGraw-Hill in 1957, there is shown and described at pages 257 et seq. a refractive index measuring technique which relies on determination of the displacement of interference fringes. Still another technique requires matching of refractive indices. These techniques usually require manual and/or visual intervention of an operator to perform the measurement, and hence are slow, cumbersome and of low resolution.

The most pertinent prior art known to applicants is U.S. Pat. No. 3,499,712 which discloses an apparatus for measuring the refractive index of a liquid sample introduced into a cell or reservoir provided in a transparent sample holder. The cell is packed with items of transparent material (e.g., spheres) that "provide at least several liquid-solid interfaces when the liquid is in contact with the packed material". The apparatus measures net transmission of light (the radiation intensity) when the cell is filled with liquid. However, that apparatus does not employ a periodic diffracting structure with high sensitivity to changes in refractive index to permit deviations from a preselected refractive index value to be noted and/or corrected.

The IBM Technical Disclosure Bulletin, Vol. 13, published June 1970, at p. 121, discloses a diffraction refractometer employing a diffraction grating immersed in a medium the refractive index of which is to be measured. This arrangement requires measurement of angles $\theta$ and $\theta'$ and hence of x and x' to calculate the refractive index. It does not sense and utilize differences in intensity of the diffracted and transmitted light.

SUMMARY OF THE INVENTION

The invention as claimed is directed to a simple, efficient, non-mechanical apparatus and method for rapidly measuring the refractive index of a fluid, whether it be a liquid or a gas. The apparatus is essentially a holographic refractometer. It determines the refractive index of a fluid sample as a function of the diffraction efficiency of light diffracted by a periodic structure of known refractive index.

According to the invention, an optical fluid analyzing apparatus and method are provided employing transparent means having a known refractive index and defining between first and second portions thereof a cell for receiving a fluid sample having an unknown refractive index. The first portion has a diffraction grating formed on its inner surface facing the cell. A light source is positioned at an incident angle with the grating to satisfy the Bragg condition. First detector means interrupts, and senses the intensity of, the light from the source that has been diffracted by the grating through the sample; and a second detector means interrupts, and senses the intensity of, the light from the source that has been transmitted by the grating through the second transparent portion. Means responsive to signals generated by the first and second detector means provides an output related to the refractive index of the sample.

BRIEF DESCRIPTION OF THE DRAWINGS

An optical fluid analyzing apparatus and method embodying the invention will now be described by way of example with reference to the accompanying drawings wherein.

DESCRIPTION OF PREFERRED EMBODIMENT

Figure 1:
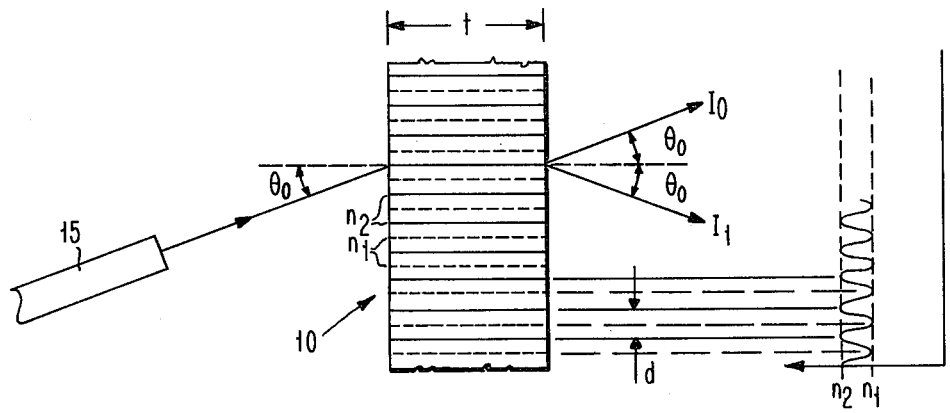
FIG. 1 is a schematic diagram depicting the manner in which light from a source is transmitted and refracted by a diffraction grating.
Figure 2:
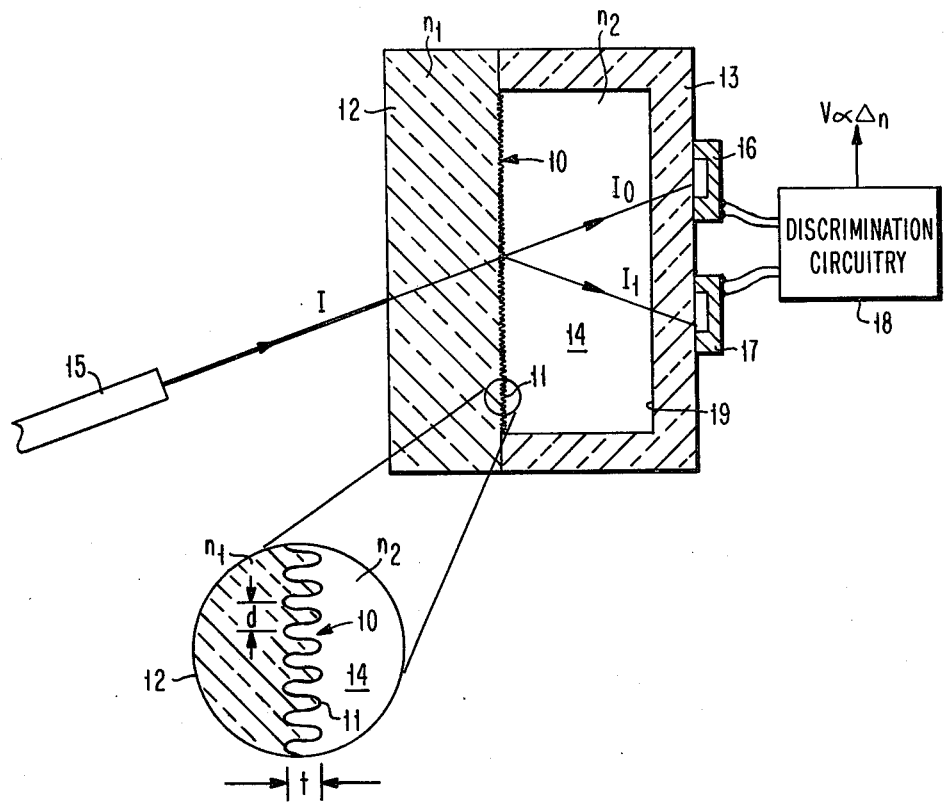
FIG. 2 is a schematic view of an optical fluid analyzing apparatus embodying the invention.

The following well-known equation defines the diffraction efficiency, $\eta$, of a periodic sinusoidal structure as:

$$\eta = \sin^2\left[\frac{\pi[\Delta n]t}{2\lambda \cos \theta_0}\right] \quad (1)$$

where, as shown in FIG. 1, $\lambda$ = wave length of the illuminating light $\theta_0$ = incident angle of the light with the structure d = period or spacing between successive nodes of the sinusoidal structure $\Delta n$ = difference in refractive index between the nodes and antinodes of the structure (i.e., between $n_1$ and $n_2$), and t = thickness of the structure As illustrated in FIG. 2, the optical fluid analyzing apparatus embodying the invention comprises a transparent diffraction grating 10 having a grating thickness t and a period or spacing d between successive nodes formed in a sinusoidal surface 11 of a transparent member 12. Member 12 and another transparent member 13 joined thereto constitute two portions of a transparent structure having a known refractive index $n_1$. The structure 12, 13 provides a chamber or cell 14 that is defined in part by the sinusoidal surface 11 of grating 10. Means (not shown) are provided for introducing into cell 14 a liquid or gaseous material having a refractive index $n_2$ that is unknown and is to be determined.

Light having a wave length $\lambda$ and an intensity I is provided by a source 15, preferably a conventional heliumneon or argon laser. The light from source 15 is directed at surface 11 of grating 10 at an incident angle $\theta_0$ to satisfy the Bragg condition:

$$\lambda = 2nd \sin \theta_0 \quad (2)$$

The diffraction efficiency, $\eta$, is defined as:

$$\eta = \frac{I_1}{I} = \frac{I_1}{I_1 + I_0} \quad (3)$$

where $I_1$ = the intensity of light diffracted by grating 10

$I_0$ = intensity of light transmitted by grating 10

A pair of detectors 16, 17, such as photo diodes, are provided to intercept the 0th order and 1st order diffracted light; i.e., to sense, respectively, the intensities $I_0$, $I_1$. These detectors provide signals to conventional discrimination circuitry 18 which combines the signals to provide a voltage V from which $\Delta n$ can be determined as follows:

$$V(\Delta n) = k\eta = k \sin^2\left[\frac{\pi[\Delta n]t}{2\lambda \cos\theta_0}\right] \quad (4)$$

where k is a constant.

In operation, assume, for sake of illustration, a refractive index variation of $\Delta n = 0.02$ which the structure 12, 13 having a grating thickness t of 4 microns is illuminated at an incident angle $\theta_0$ of 20° with light at a wave length $\lambda$ of 488 nanometers. Under this assumed condition, diffraction efficiency $\eta$ would be equal to 0.073 (7.3%).

By way of contrast, if the index matching technique were used, the efficiency $\eta$ of light reflected from an interface of index difference 0.02 would be:

$$\eta = \left[\frac{n_1 - n_2}{n_1 + n_2}\right]^2 = 4.4 \times 10^{-5} \quad (5)$$

over 3 orders of magnitude smaller.

The apparatus embodying the invention can be used to measure the refractive index of a liquid or gas which fills cell 14 or is caused to flow continuously through the cell. If the size of cell 14 is reduced so that the inner wall 19 of member 13 substantially abuts the sinusoidal surface 11 of grating 10, the material having the unknown or variable refractive index may be introduced into the structure 12, 13 by capillary action. The volume of cell 14 can be extremely small because only the grooves in surface 11 need be filled.

It will be understood that the analyzing apparatus herein discussed may be used to indicate the state or status of a fluid medium, or used in conjunction with a servo system to adjust certain parameters to maintain the fluid in a preselected condition. For example, the apparatus can be used to monitor the state of charge of an electrolyte. The difference in refractive index between a fully charged and a fully discharged electrolyte has been determined to be in the order of about $\Delta n = 0.02$. Hence, by providing a transparent structure 12, 13 having an index matched with the charged state, no diffraction will occur. However, as discharge occurs, more and more light will be diffracted, and a voltage signal representing the state of charge can be derived using equation (4). In the fully discharged state, 7.3% of the light will be in the first order.

Use of a conventional laser 15 as the light source provides a very accurate system. However, if preferred, a light emitting diode and collemating lens (not shown) positioned to satisfy the Bragg condition could be substituted for laser 15 because the lack of coherence would merely cause a blurring of the image and not a significant loss in efficiency. Also, the detectors 16, 17 for convenience (provided the size of the structure 12, 13 permits) may be mounted on an exterior surface 20 of member 13, as shown. However, if preferred, the detectors 16, 17 may be separate from the structure 12, 13. The grating 10 is preferably made by holographic recording as a surface relief in a photoresist or similar material and subsequently pressed or replicated into a transparent substitute of appropriate refractive index.

While the invention has been shown and described with reference to a preferred embodiment thereof, it will be understood by those skilled in the art that the foregoing and other changes in form and detail may be made therein without departing from the spirit, scope and teaching of the invention. Accordingly, the apparatus and method herein disclosed are to be considered merely as illustrative and the invention is to be limited only as specified in the claims.

We claim:

1. An optical fluid analyzing apparatus comprising:
    transparent means having a known refractive index and defining between first and second portions thereof a cell for receiving a fluid sample having an unknown refractive index, said first portion having a diffraction grating formed on an inner surface facing the cell;
    a light source positioned at an incident angle with said grating to satisfy the Bragg condition;
    first detector means for sensing the intensity of the light from said source that has been diffracted by said grating through the sample;
    second detector means for sensing the intensity of the light from said source that has been transmitted by said grating through said second transparent portion;
    and
    means responsive to signals generated by said first and second detector means for providing an output related to the refractive index of the sample.

2. An apparatus according to claim 1, characterized in that said responsive means includes
    means providing a voltage signal proportional to the difference in the refractive index between nodes and antinodes of the grating; and
    means for calculating the unknown refractive index using said difference.

3. An apparatus according to claim 1, characterized in that said first and second detector means are mounted on an exterior surface of said second transparent portion.

4. An apparatus according to claim 1, characterized by the light source being a coherent light source, such as a laser.

5. An apparatus according to claim 1, characterized by the light source comprising a light emitting diode and collimating lens.

6. An apparatus according to claim 1, further characterized in that the inner surface of said second transparent portion substantially contacts the grating forming part of said first transparent portion, for causing the cell to be defined substantially solely by channels in said grating, thereby to cause the fluid to be sampled to be drawn through the channels by capillary action.

7. A method of optically analyzing a fluid sample of unknown refractive index, comprising the steps of:
    introducing the sample to a cell defined between two portions of a transparent structure having a known refractive index, the cell being defined between a diffraction grating forming part of an inner surface of one of the transparent portions and the adjacent inner surface of the other transparent portion;
    passing light from a source at an incident angle with said grating to satisfy the Bragg condition;
    providing a pair of detectors for intercepting and sensing the intensities of the light from said source that has been (a) diffracted by the grating through the sample and (b) transmitted by said grating through the second transparent portion, respectively; and
    determining the refractive index of the sample from signals generated by the pair of detectors.

* * * * *